(12) United States Patent
Gianchandani et al.

(10) Patent No.: US 7,452,334 B2
(45) Date of Patent: * Nov. 18, 2008

(54) ANTENNA STENT DEVICE FOR WIRELESS, INTRALUMINAL MONITORING

(75) Inventors: Yogesh B. Gianchandani, Ann Arbor, MI (US); Kenichi Takahata, Ann Arbor, MI (US); Kensall D. Wise, Ann Arbor, MI (US); Andrew D. DeHennis, Germantown, MD (US)

(73) Assignee: The Regents of The University of Michigan, Ann Arbor, MI (US)

( * ) Notice: Subject to any disclaimer, the term of this patent is extended or adjusted under 35 U.S.C. 154(b) by 342 days.

This patent is subject to a terminal disclaimer.

(21) Appl. No.: 10/939,684

(22) Filed: Sep. 13, 2004

(65) Prior Publication Data

US 2005/0080346 A1    Apr. 14, 2005

Related U.S. Application Data

(63) Continuation-in-part of application No. 10/737,314, filed on Dec. 16, 2003.

(60) Provisional application No. 60/502,410, filed on Sep. 12, 2003, provisional application No. 60/433,846, filed on Dec. 16, 2002.

(51) Int. Cl.
*A61B 5/02* (2006.01)
*A61F 2/06* (2006.01)

(52) U.S. Cl. ...................... 600/485; 623/1.15
(58) Field of Classification Search ....... 623/1.11–1.54; 600/504, 485
See application file for complete search history.

(56) References Cited

U.S. PATENT DOCUMENTS

| 6,015,387 | A | 1/2000 | Schwartz et al. |
|---|---|---|---|
| 6,053,873 | A | 4/2000 | Govari et al. |
| 6,086,604 | A | 7/2000 | Fischell et al. |
| 6,206,835 | B1 | 3/2001 | Spillman, Jr. et al. |
| 6,206,914 | B1 * | 3/2001 | Soykan et al. ............... 623/1.42 |
| 6,231,516 | B1 * | 5/2001 | Keilman et al. ............. 600/485 |
| 6,278,379 | B1 | 8/2001 | Allen et al. |
| 6,442,413 | B1 | 8/2002 | Silver |
| 6,586,699 | B1 | 7/2003 | Gianchandani et al. |
| 6,592,518 | B2 | 7/2003 | Denker et al. |

(Continued)

OTHER PUBLICATIONS

International Search Report corresponding to International Patent Application Serial No. PCT/US03/40225, European Patent Office, dated Jun. 21, 2004, 7 pages.

(Continued)

*Primary Examiner*—Suzette J Gherbi
(74) *Attorney, Agent, or Firm*—Marshall, Gerstein & Borun LLP (57) ABSTRACT

Disclosed herein is a stent device useful for maintaining the patency of a lumen while monitoring an intraluminal characteristic. The device includes a structure having a set of extendible bands that are capable of plastic deformation to form a scaffolding having an inductance, and further includes a capacitance coupled to the set of extendible bands and responsive to the intraluminal characteristic. The capacitance and the inductance form a tank circuit after the plastic deformation of the set of extendible bands to enable wireless transmission of an indication of the intraluminal characteristic.

61 Claims, 4 Drawing Sheets

U.S. PATENT DOCUMENTS

| | | | |
|---|---|---|---|
| 6,624,377 | B2 | 9/2003 | Gianchandani et al. |
| 6,729,336 | B2 | 5/2004 | Da Silva et al. |
| 6,802,857 | B1* | 10/2004 | Walsh et al. ............... 623/1.15 |
| 6,926,670 | B2 | 8/2005 | Rich et al. |
| 2002/0156525 | A1 | 10/2002 | Smith et al. |
| 2002/0173839 | A1 | 11/2002 | Leopold et al. |
| 2002/0179573 | A1 | 12/2002 | Gianchandani et al. |
| 2002/0188345 | A1 | 12/2002 | Pacetti |
| 2004/0149294 | A1* | 8/2004 | Gianchandani et al. ..... 128/879 |
| 2006/0265049 | A1* | 11/2006 | Gray et al. ................. 623/1.16 |
| 2007/0213809 | A1* | 9/2007 | Weber ....................... 623/1.15 |

OTHER PUBLICATIONS

Leung, M.D. et al., "Selection Of Stents For Treating Iliac Arterial Occlusive Disease," J. Vasc. Interv. Radiol., vol. 14, No. 2, Feb. 2003, pp. 137-152.

Anderson, P.E., "Carotid Artery Stenting," J. Intrv. Radiol, vol. 13, No. 3, 1998, Abstract.

Rees, C.R., "Stents For Atherosclerotic Renovascular Disease," J. Vasc. Interv. Radiol., vol. 10, No. 6, 1999, Abstract.

Mueller, Pena C., "Metallic Stents In The Biliary Tree," Min. Invas. Ther. & Allied Technol., vol. 8, No. 3, 1999, Abstract.

Auge, B.K. et al., "Ureteral Stents And Their Use In Endourology," Curr. Opin. Urol., vol. 12, No. 3, 2002, Abstract.

Kathuria, Y.P., "Laser Microprocessing Of Stent For Medical Therapy," Proc. IEEE Micromech. Human SCI., Japan, 1998, pp. 111-114.

Takahata, Kenichi et al., "Batch Mode Micro-Electro-Discharge Machining," Journal Of Microelectromechanical Systems, vol. 11, No. 2, Apr. 2002, pp. 102-110.

Takahata, Kenichi et al., "Coronary Artery Stents Microfabricated From Planar Metal Foil: Design, Fabrication And Mechanical Testing," Proce. IEEE MEMS, Jan. 2003, pp. 462-465.

Conti, JC et al., "The Durability Of Silicone Versus Latex Mock Arteries," Proc. ISA Biomed, SCI. Instrum. Symp., vol. 37, 2001, pp. 305-312.

Chua, S.N. David et al., "Finite-Element Simulation Of Stent Expansion," Journal Of Materials Processing Technology, vol. 120, 2002, pp. 335-340.

Flueckiger M.D., Fritz et al., "Strength, Elasticity, And Plasticity Of Expandable Metal Stents: In Vitro Studies With Three Types Of Stress," J. Vasc. Interv. Radiol., vol. 5, No. 5, 1994, pp. 745-750.

Rieu, Regis et al., "Radial Force Of Coronary Stents: A Comparative Analysis," Catheter. Cardiovasc. Interv., vol. 46, 1999, pp. 380-391.

Shoji, Shuichi et al., "Fabrication Of An Impantable Capacitive Type Pressure Sensor," Dept. of Electronic Engineering, Tohoku University, Sendai 980, Japan, Proc. $4^{th}$ Int. Conf. Solid-State Sensor and Actuators (1987) pp. 305-308.

Miao, Chih-Lei et al., "Body Position And Pressure Distribution Sensors In Prosthetic Systems For Computer-Controlled Walking," Proc. $4^{th}$ Int. Conf. Solid-State Sensor and Actuators (1987), pp. 57-60.

Akin, Tayfun et al., "RF Telemetry Powering And Control Of Hermetically Sealed Integrated Sensors And Actuators," Center For Integrated Sensors And Circuits, Dept. of Electrical. Engineering And Computer Science, University of Michigan, IEEE, 1990, pp. 145-148.

Ziaie, Babak et al., "A High-Current IrOx Thin-Film Neuromuscular Microstimulator," Center for Integrated Sensors And Circuits, Dept. of Electrical Engineering And Computer Science, University of Michigan, IEEE, 1991, pp. 124-127.

Spillman, Jr., William B., "Sensing And Processing For Smart Structures," Proceedings of the IEEE, vol. 84, No. 1, Jan. 1996, pp. 68-77.

International Search Report for PCT/US2005/19819, mailed Sep. 6, 2006.

Written Opinion of the International Searching Authority for PCT/US2005/19819, mailed Sep. 6, 2006.

Akar et al., "A wireless batch sealed absolute capacitive pressure sensor," Sensors and Actuators A, 95, pp. 29-38 (2001).

DeHennis et al., "A double-sided single-chip wireless pressure sensor," Proc. IEEE MEMS 2002, pp. 252-255 (2002).

E. Park et al., "Hermetically Sealed Inductor-Capacitor (LC) Resonator for Remote Pressure Monitoring," Jpn. J. Appl. Phys., vol. 37, pp. 7124-7128 (1998).

* cited by examiner

ANTENNA STENT DEVICE FOR WIRELESS, INTRALUMINAL MONITORING

RELATED APPLICATIONS

This application claims the benefit of provisional application Ser. No. 60/502,410, filed on Sep. 12, 2003, and entitled "Micromachined Stent that Serves as an Antenna for Monitoring Implantable Microsensors," and is a continuation-in-part of co-pending and commonly assigned application Ser. No. 10/737,314, filed on Dec. 16, 2003, and entitled "Assembly And Planar Structure For Use Therein Which Is Expandable Into A 3-D Structure Such As A Stent And Device For Making The Planar Structure," which, in turn, claims the benefit of provisional application Ser. No. 60/433,846, filed on Dec. 16, 2002, and entitled "Design and Fabrication of Stent Using Planar Metal Foils."

STATEMENT REGARDING FEDERALLY SPONSORED RESEARCH OR DEVELOPMENT

This invention was made with government support under Award No.: ECS-0233174 from the National Science Foundation. The government has certain rights in the invention.

BACKGROUND OF THE INVENTION

1. Field of the Invention

The invention generally relates to intraluminal devices and, more particularly, devices used to monitor intraluminal characteristics.

2. Brief Description of Related Technology

In recent years, stents have come to play an essential role in the treatment of cardiovascular diseases. A stent typically has mesh-like walls in a tubular shape, and once positioned by a catheter, is expanded radially by the inflation of an angioplasty balloon. Stents are implanted by such procedures to physically expand and scaffold coronary and other arteries that have been narrowed by plaque. However, re-closures often occur due to recoil of the blood vessels, further plaque deposition, or spasms.

Monitoring of blood flow can provide advance notice of such failures and, thus, continuing measurement of blood flow is therefore important for long-term monitoring of vascular diseases. Implantable pressure sensors are promising devices for continuous monitoring of blood pressure and flow rate, and could provide advance notice of restenosis, which is a common failure mechanism for stents. Detection mechanisms proposed in the past for implantable sensors include thermal resistor, blood conductivity, and differential pressure measurement using capacitive diaphragms.

Wireless monitoring of cardiac parameters has been used to ease the delivery of information from implanted measurement devices. Passive telemetric sensing of pressure has been implemented using an implanted microchip with a planar thin film inductor fabricated together with a micromachined capacitive pressure sensor. See, for example, E. Park, et al., "Hermetically Sealed Inductor-Capacitor (LC) Resonator for Remote Pressure Monitoring," Jpn. J. Appl. Phys., Vol. 37, pp. 7124-28 (1998). This L-C tank circuit couples to a separate, external transmitting coil via mutual inductance. The change in pressure can be detected by the shift in frequency at which the external coil shows a characteristic dip in impedance and phase.

Despite these advances in implantable devices and wireless monitoring methods, the implementation and deployment of such devices is complicated by the presence of the thin-film inductor necessary for passive telemetry. The prior art also does not sufficiently teach or suggest to one of ordinary skill in the art how to utilize stents, of either existing or novel design, in the implementation, deployment and operation of such implantable measurement devices. Still further, the prior art does not sufficiently teach or suggest to one of ordinary skill in the art a stent device capable of maintaining the patency of a lumen while also monitoring one or more intraluminal characteristics.

SUMMARY OF THE INVENTION

In accordance with one aspect, disclosed herein is a stent device including a structure having a set of extendible bands that are capable of plastic deformation to form a scaffolding having an inductance, and a capacitance coupled to the set of extendible bands such that the capacitance and the inductance form a tank circuit after the plastic deformation of the set of extendible bands.

In one embodiment, the structure comprises a longitudinal beam coupled to the set of extendible bands. The longitudinal beam may include a side beam having a reduced-width link between adjacent bands of the set of extendible bands such that the reduced-width link breaks a connection between the adjacent bands upon plastic deformation of the structure. Alternatively, the longitudinal beam and the set of extendible bands are directly connected by a single link.

In another embodiment, the structure includes a further set of extendible bands such that the scaffolding includes a further inductance. The stent device then includes a further capacitance coupled to the further set of extendible bands such that the further capacitance and the further inductance form a further tank circuit after plastic deformation of the further set of extendible bands. The longitudinal beam may then be a common electrical node for the first-named and further named inductances and the first-named and further named capacitances. The first-named and further capacitances may include first and second capacitive sensors, respectively, and the first and second capacitive sensors may be disposed at opposite ends of the longitudinal beam. The opposite ends of the longitudinal beam may be positioned beyond where an expandable deployment device is disposed during the plastic deformation of the structure. The structure may include first and second platforms upon which the first and second capacitive sensors are mounted, respectively.

In an alternative embodiment, the set of extendible bands includes a non-conductive support and a conductive trace disposed on the non-conductive support.

The scaffolding may include a helix portion and a ring portion such that the ring portion provides structural support at an end of the helix portion. The set of extendible bands may have a non-helical configuration prior to the plastic deformation and a portion of the non-helical configuration may form the scaffolding upon deployment. The non-helical configuration may be planar such that each extendible band of the set of extendible bands includes a plurality of involute, planar sections prior to plastic deformation. Alternatively, the non-helical configuration is tubular.

In accordance with another aspect, disclosed is a device useful for maintaining patency of a lumen while monitoring ah intraluminal characteristic of the lumen. The device has a sensor responsive to the intraluminal characteristic of the lumen to generate a signal indicative thereof, and a stent structure having a non-helical configuration prior to deployment. The non-helical configuration of the stent structure is capable of plastic deformation to form a helical scaffolding upon deployment such that the helical scaffolding includes an inductance coupled to the sensor for wireless transmission of the signal.

In one embodiment, the non-helical configuration includes a planar set of involute bands. Alternatively, the non-helical configuration includes a plurality of cross bands coupled via a beam having a breakable link for disconnecting adjacent cross bands of the plurality of cross bands upon deployment to form the helical scaffolding. The stent structure may be further capable of plastic deformation to form a non-helical scaffolding structurally coupled to the helical scaffolding for maintaining the patency of the lumen. The non-helical scaffolding may include a pair of rings coupled to the helical scaffolding at respective longitudinal ends of the helical scaffolding.

In accordance with another aspect, a device for maintaining patency of a lumen while monitoring an intraluminal characteristic of the lumen includes a sensor and a scaffolding. The sensor is responsive to the intraluminal characteristic of the lumen to generate a signal indicative thereof, and the scaffolding is deployed in the lumen and has a helical portion and a non-helical portion. The helical portion includes an inductance coupled to the sensor for wireless transmission of the signal and the non-helical portion provides structural support for maintaining the patency of the lumen.

In one embodiment, the helical and non-helical portions of the scaffolding are formed of a continuous tubular sheet.

In accordance with yet another aspect, a stent device for monitoring an intraluminal characteristic includes a plastically deformable structure having a helical portion upon catheter-based deployment. The plastically deformable structure includes a sensor site positioned at an end of the plastically deformable structure. The stent device further includes a sensor capable of generating a signal indicative of the intraluminal characteristic. The sensor is structurally coupled to the plastically deformable structure at the sensor site such that the sensor is suitably disposed for the catheter-based deployment with the plastically deformable structure. The helical portion has an inductance coupled to the sensor to enable wireless transmission of the signal generated by the sensor.

In one embodiment, the end lies beyond an extent reached by an inflatable deployment device used during the catheter-based deployment. The sensor site may include a platform upon which the sensor is mounted. The plastically deformable structure and the platform may be formed of a continuous, conductive sheet such that the plastically deformable structure is capable of residing in a non-helical profile that enables catheter-based deployment. The platform and the sensor may be rigidly bonded such that the sensor is protected from damage from bending forces experienced during the catheter-based deployment.

In accordance with still another aspect, a stent device useful for monitoring first and second intraluminal characteristics includes first and second sensors generating respective signals indicative of the first and second intraluminal characteristics, respectively. The stent device further includes a scaffolding having first and second inductive coils respectively coupled to the first and second sensors for separate, wireless transmission of the respective signals indicative of the first and second intraluminal characteristics.

In one embodiment, the stent device further includes first and second platforms upon which the first and second sensors are mounted, respectively. The first and second platforms are spaced upstream and downstream from the scaffolding via first and second interconnects, respectively.

BRIEF DESCRIPTION OF THE DRAWING FIGURES

For a more complete understanding of the invention, reference should be made to the following detailed description and accompanying drawing in which like reference numerals identify like elements in the several figures, and in which.

While the disclosed stent device is susceptible of embodiments in various forms, there are illustrated in the drawing (and will hereafter be described) specific embodiments of the invention, with the understanding that the disclosure is intended to be illustrative, and is not intended to limit the invention to the specific embodiments described and illustrated herein

DETAILED DESCRIPTION OF THE INVENTION

Disclosed herein is a stent device designed to both maintain the patency of a lumen and monitor an intraluminal characteristic of the lumen in which it is deployed. Generally speaking, the stent device incorporates one or more integrated antennas for telemetric communication of signals developed by one or more sensors. The antenna is integrated in the sense that the scaffolding that provides structural support also includes one or more inductances in the form of one or more helical coils.

In certain embodiments, the helical configuration of the scaffolding is formed from a set of extendible bands capable of plastic deformation from a planar or non-helical configuration that simplifies fabrication. The low-profile of the planar configuration also simplifies deployment via catheter-based techniques. For these reasons, practice of the disclosed stent device is particularly well suited for use as a coronary artery stent, where the sensor(s) may be used for monitoring pressure or flow in the artery in which the stent device and sensor(s) are implanted. In one embodiment, multiple sensors are supported by the disclosed stent device, such that two micromachined pressure sensors are deployed at opposite ends of the device for a differential pressure measurement. The upstream and downstream locations of the two sensors, and the resulting differential pressure measurement, are well suited for providing an indication of how well the stent is maintaining the patency of the artery. In this way, the stent device provides a direct and continuous indication of whether restenosis is occurring at the stent site.

Although the stent device is described herein in detail in the context of arterial applications, practice of the disclosed device is not limited thereto, and may be applied in many other contexts. Possible contexts include a number of other non-arterial passages, such as respiratory passages, pancreatic ducts, lymphatic ducts, urinary tracts, biliary tracts, and the like. However, practice of the disclosed device is not limited to biomedical applications, but rather further includes non-biomedical contexts, such as tire pressure monitoring within a tire stem, and other applications where a lumen or other tubular structure may benefit from structural support, wireless monitoring, or both. Accordingly, terms such as "lumen" and "patency" are used herein without any implication that practice of the disclosed device is limited to a particular context or application.

The disclosed device is compatible with a number of fabrication processes, materials, and stent designs. In one embodiment, the disclosed device is advantageously formed as a micromachined stent, but fabrication of the disclosed device is certainly not limited to any one micromachining fabrication process. More particularly, the disclosed device is compatible with, and described herein in connection with, high-volume, batch-manufacturable micro electro-discharge machining (μEDM) fabrication processes, but other processes, such as laser-based machining techniques, are compatible as well. For instance, such laser-based techniques may even be relied upon in embodiments where the scaffolding structure is formed from a pre-existing stent, such as one manufactured from tubular stainless steel, where the laser is used to selectively cut certain links to create an inductive pattern. The μEDM fabrication process is described in detail in co-pending and commonly assigned application Ser. No. 10/737,314, filed on Dec. 16, 2003, and entitled "Assembly And Planar Structure For Use Therein Which Is Expandable Into A 3-D Structure Such As A Stent And Device For Making The Planar Structure," the disclosure of which is hereby incorporated by reference in its entirety. See also, for example, Takahata et al., "Coronary Artery Stents Microfabricated From Planar Metal Foil: Design, Fabrication, and Mechanical Testing," IEEE Conf. MEMS, pp. 462-465 (2003), the teachings and disclosure of which are also hereby incorporated by reference.

The μEDM fabrication process described in the referenced materials advantageously relies upon planar metal foil or sheets as a starting material, but other materials and other shapes (e.g., tubular metal sheets) may be used to fabricate the disclosed device. In these embodiments, the structural material of the stent, e.g., stainless steel, also provides the electrical connections necessary for operation. However, in alternative embodiments, electrical traces may be disposed on a different material, such as a dielectric, used as a non-conductive structural support. In such cases, the shape of the inductance(s) is not as limited to the shape of the structural support.

Generally speaking, monitoring functionality is imparted to a stent such that the disclosed stent device has improved electrical characteristics upon deployment through, for instance, balloon angioplasty. In fact, in certain embodiments, the act of deployment may automatically transform the electrical characteristics of the stent such that inductive properties are present. More generally, however, the stent device presents one or more inductances sufficient for wireless transmission of signals developed by one or more sensors respectively coupled to the inductances.

Figure 1:
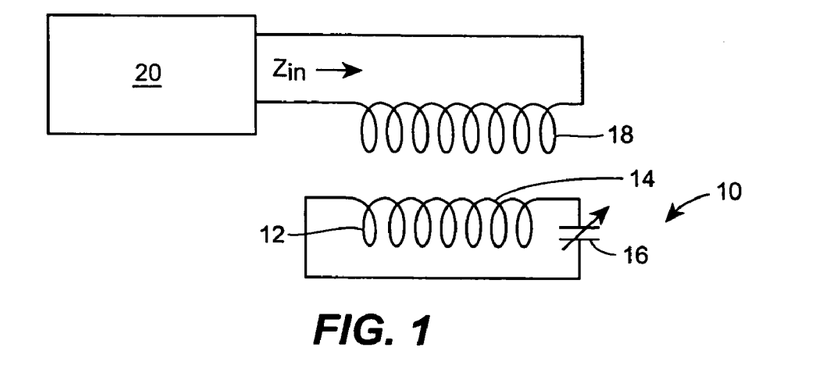
FIG. 1 is a schematic representation of an intraluminal monitoring system having a stent device in accordance with one embodiment.

With reference now to FIG. 1, the manner in which such wireless transmission is accomplished is shown in a system-level schematic in accordance with one embodiment of the disclosed device. A stent device generally indicated at 10 is deployed or implanted in an artery or other lumen (not shown) such that a scaffolding 12 has expanded within the artery to form a number of coils 14 in a helical portion thereof. The scaffolding 12 may provide structural support to maintain the patency of the artery and, to that end, may include non-helical portions other than the coils 14, as will be described in greater detail. Generally speaking, however, the scaffolding includes an inductance provided by the coils 14 that is electrically connected to a capacitive element 16. In this embodiment, the capacitive element 16 has a capacitance that varies with the pressure inside the artery. More generally, however, the inductance provided by the coils 14 is connected within a tank circuit (e.g., an LC tank circuit) that resonates at a frequency determined by the measurement taken by a sensor responsive to an intraluminal characteristic, such as arterial pressure. In this way, the sensor may take a number of different forms, and need not rely on variable capacitance to generate an indication of the intraluminal characteristic. For instance, the capacitive element 16 may instead simply provide the capacitive element of a tank circuit having a resistive sensor, another capacitive sensor, or other configurations that may occur to one skilled in the art.

As shown in the embodiment of FIG. 1, the tank circuit is an LC tank circuit having a capacitive sensor in the interest of minimizing the power consumed by the elements of the passive tank circuit during operation. In addition to passive telemetric communication of the intraluminal characteristic, power is transmitted wirelessly to the tank circuit from a separate, external transmitting coil 18. In this embodiment, the tank circuit wirelessly loads down the coil 18 such that a change in pressure within the artery can be detected by a shift in the frequency at which the coil 18 shows a characteristic dip in impedance. This frequency shift or impedance change may be detected through a spectrum analyzer 20 or other device well known to those skilled in the art. As is also well known, the spectrum analyzer 20 may also include a signal generator.

In the passive telemetry embodiment of FIG. 1, both the coil 18 and the spectrum analyzer 20 and, consequently, the power source, conveniently reside outside of the body or other structure in which the artery is located. Despite the benefits of enabling passive wireless monitoring, practice of the disclosed device is not limited to passive telemetric applications. Active telemetric methods may also benefit from the inductance provided by the scaffolding 12 where any one of a number of load modulation techniques, some of which may involve an implanted chip either integrated with, or discrete from, any implanted sensor, may provide improved transmission of data from the sensor.

Figure 2A:
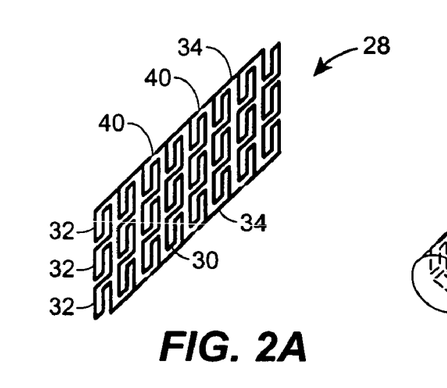
FIGS. 2A-2D are schematic representations of the stent device of FIG. 1 in accordance with an embodiment having links breakable upon deployment.

The manner in which the scaffolding 12 has a helical portion to form an inductive coil will now be described in greater detail in connection with the embodiment shown in FIGS. 2A-D. First, by way of background, most commercially-available stents are made from laser-machined stainless steel tubes. While the disclosed device may also be formed from such tubes, stents cut from planar metal foils by μEDM fabrication offer very good mechanical properties. Further, this approach permits the stent devices to be fabricated from the metallic (e.g., steel) foil with high throughput and precision by using planar electrodes as cookie-cutters that have been lithographically patterned on a silicon wafer. These stent devices use flexural designs and do not have any bonded or welded seams and, thus, will be relied upon in this embodiment. With reference to FIG. 2A, a stent device indicated generally at 28 is micromachined from a planar metal foil into a set of extendible bands 30 where each extendible band 30 includes a plurality of involute, planar sections 32 prior to plastic deformation. The extendible bands 30 are connected and supported by a pair of longitudinal side beams 34.

The set of extendible bands 30 and, accordingly, the plurality of involute, planar sections 32 form a planar structure, which is expandable into a 3-D structure. The planar structure may plastically deform during expansion so that the 3-D structure is free-standing. More particularly, a first set of the bands are expandable in a first direction, while a second set of the bands may be expandable in a second direction substantially opposite the first direction to form a mesh-like 3-D structure. To this end, adjacent bands may be expandable in the opposite directions.

Figure 2B:
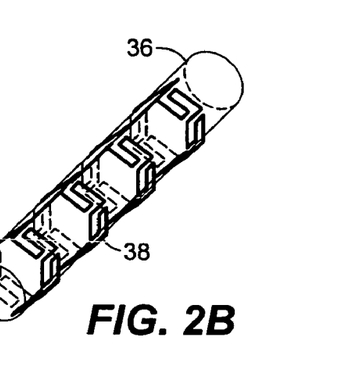

In assembling the device as shown in FIG. 2B, a deflated angioplasty balloon 36 is threaded alternately above and below adjacent bands 30, and then expanded by normal angioplasty procedure. Prior to expansion, however, the intermediate structure of FIG. 2B is essentially a set of series-connected rings 38, which offers negligible inductance.

Figure 2C:
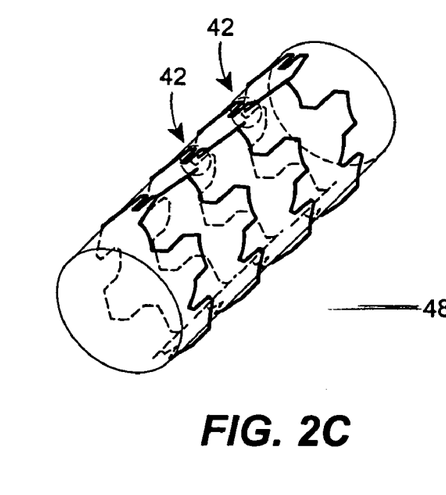
Figure 2D:
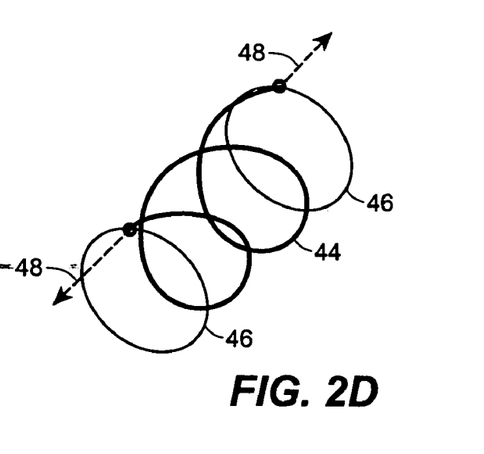

For the stent scaffolding to serve as an antenna, its overall shape should follow the pattern of a helical coil. However, the planar pattern of a helical coil does not provide sufficient mechanical robustness for subsequent handling during assembly and deployment. This challenge is addressed by inserting breakable links 40 at select locations in the side beams 34 (see FIG. 2A). These links 40 may be created by narrowing the width of the beam to create stress concentrations that ultimately fracture at certain locations when the balloon is inflated, as shown in FIG. 2C. Prior to balloon inflation, the links 40, along with the rest of the structure, provide the mechanical strength to hold the structure tightly around the balloon 36 during assembly and while it is being positioned with a catheter (not shown). When the balloon 36 is expanded for deployment of the stent device 28 as shown in FIG. 2C, torsional strain developed in the side beams 34 is effectively concentrated at the links 40, leading to fracture and a selective disconnection 42 of the side beam 34, and resulting in a final shape that has a portion of essentially helical shape. The final shape of the stent device 28 is simplified for purposes of illustration in FIG. 2D, where a helical portion 44 of the scaffolding is disposed between, and structurally coupled to, two end portions 46 of a non-helical, ring-like shape. The ring-shaped end portions 46 at each longitudinal end of the device 28 provide further structural support to maintain the patency of the lumen, while the helical portion 44 provides the inductance to complete the tank circuit (FIG. 1). Electrical leads 48 provide electrical connections for the helical coil to the remainder of the tank circuit.

The stent device shown in FIGS. 2A-D may be fabricated from 50 μm-thick type 304 stainless steel foil and expanded with a standard balloon catheter. It should be noted that, although the extendible bands 30 of the embodiment shown in FIGS. 2A-D have structural beams with a square cross section, the beams can be rounded by electrochemical polishing. In one example of the embodiment of FIGS. 2A-D, the length, diameter and number of turns are 4 mm, 3.5 mm, and 1.5, respectively. In this case, the measured inductance changes from an undetectable level to 20 nH upon expansion. Further information regarding this exemplary stent device 28 and its operation in a tank circuit with a capacitive pressure sensor is set forth herein below as Example 1.

In summary, the stent device 28 of FIGS. 2A-D demonstrates that a stent structure can be obtained by plastically reshaping a planar microstructure which is cut from planar metal foil and expanded into a tubular shape by inflation of an angioplasty balloon on which the device is mounted. The stent device 28, fabricated by batch-compatible μEDM, was found to offer sufficient radial strength and axial compliance. To transform these stents from mere mechanical devices, the breakable links 40 are relied upon to form the inductive coil 44 as it was expanded through deployment. This technique allowed the stent device 28, when coupled to a capacitive sensor as shown in FIG. 1, to serve as the antenna that enables the telemetric measurement of pressure (see Example 1).

Figure 3:
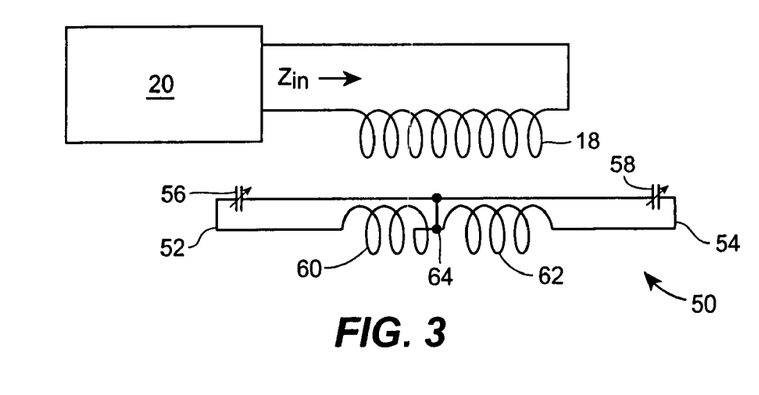
FIG. 3 is a schematic representation of an intraluminal monitoring system having a stent device in accordance with another embodiment having multiple sensors.

In an alternative embodiment capable of supporting intraluminal monitoring such as pressure and flow measurement, a dual-inductor stent device indicated generally at 50 is shown schematically in FIG. 3 as integrated in first and second tank circuits 52 and 54 having first and second capacitive sensors 56 and 58, respectively. Generally speaking, dual-inductor stent devices utilize the two tank circuits 52 and 54 to enable separate, wireless transmission of two signals, thereby providing separate indications of two intraluminal characteristics. In one exemplary embodiment, the two sensors 56 and 58 are located at opposite longitudinal ends of the device, such that one of the two sensors 56 and 58 is disposed at an upstream location, while the other is disposed at a downstream location. Elements similar to those shown in prior figures are indicated with like reference numerals.

The dual-inductor configuration offers operational advantages in arterial and other applications where, for instance, the back pressure will depend on arterial location as well as physical condition of the patient. The differential measurement of two resonant peaks associated with the two separate LC tanks 52 and 54 at different locations can overcome the limitations of single-point measurements. More generally, however, the integration of the dual-inductor stent device 50 with two Si micromachined capacitive pressure sensors as the sensors 56 and 58 will enable the implementation of a wireless flow-sensing system offering high sensitivity.

In the exemplary embodiments schematically shown in FIG. 3, the stent device 50 is shown as having two separate coils 60 and 62 for the LC tanks 52 and 54, respectively. While this may indeed be the case, in one embodiment, the coils 60 and 62 may be formed from a single helical portion of the stent scaffolding, but with a tap 64 that is either centered or positioned off-center. The advantage of an off-center positioning is that the coils 60 and 62 will not have an equal number of turns. Thus, the respective LC tanks 52 and 54 will transmit at the aforementioned two resonant peaks, thereby enabling two separate measurements from the two sensors 56 and 58. In the exemplary embodiment of FIG. 3, the coil 60 has three turns, while the coil 62 has three-and-one-half turns.

Figure 4:
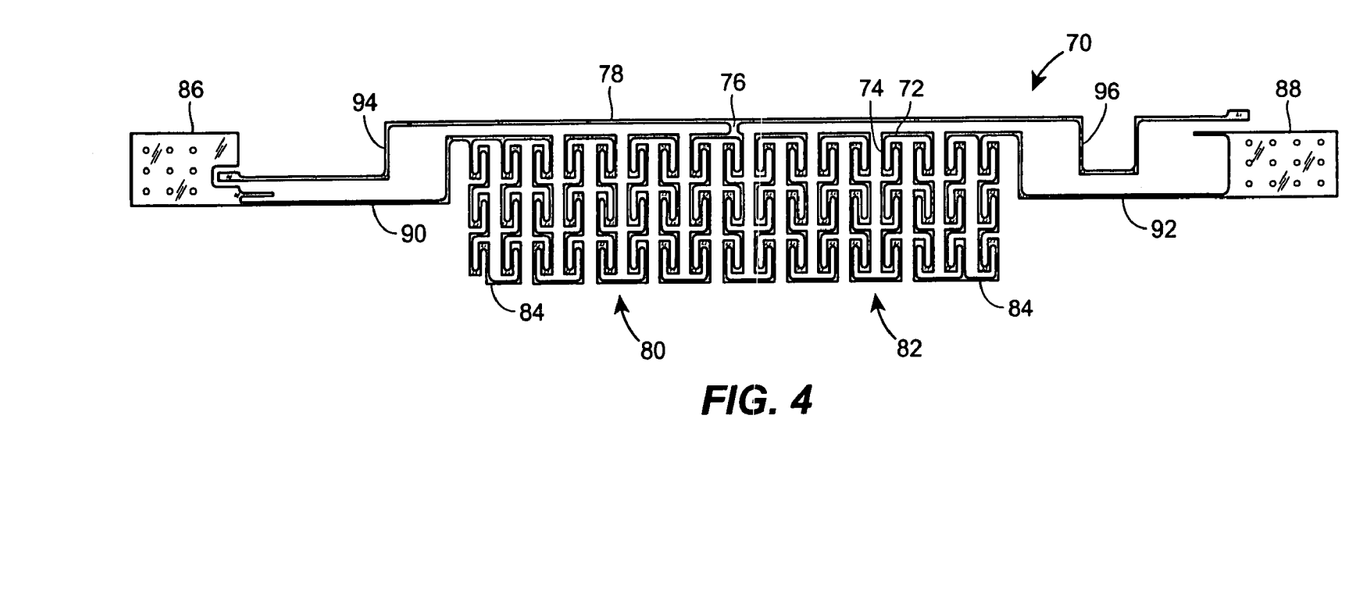
FIG. 4 is a plan view of the stent device of FIG. 3.
Figures 5, 6:
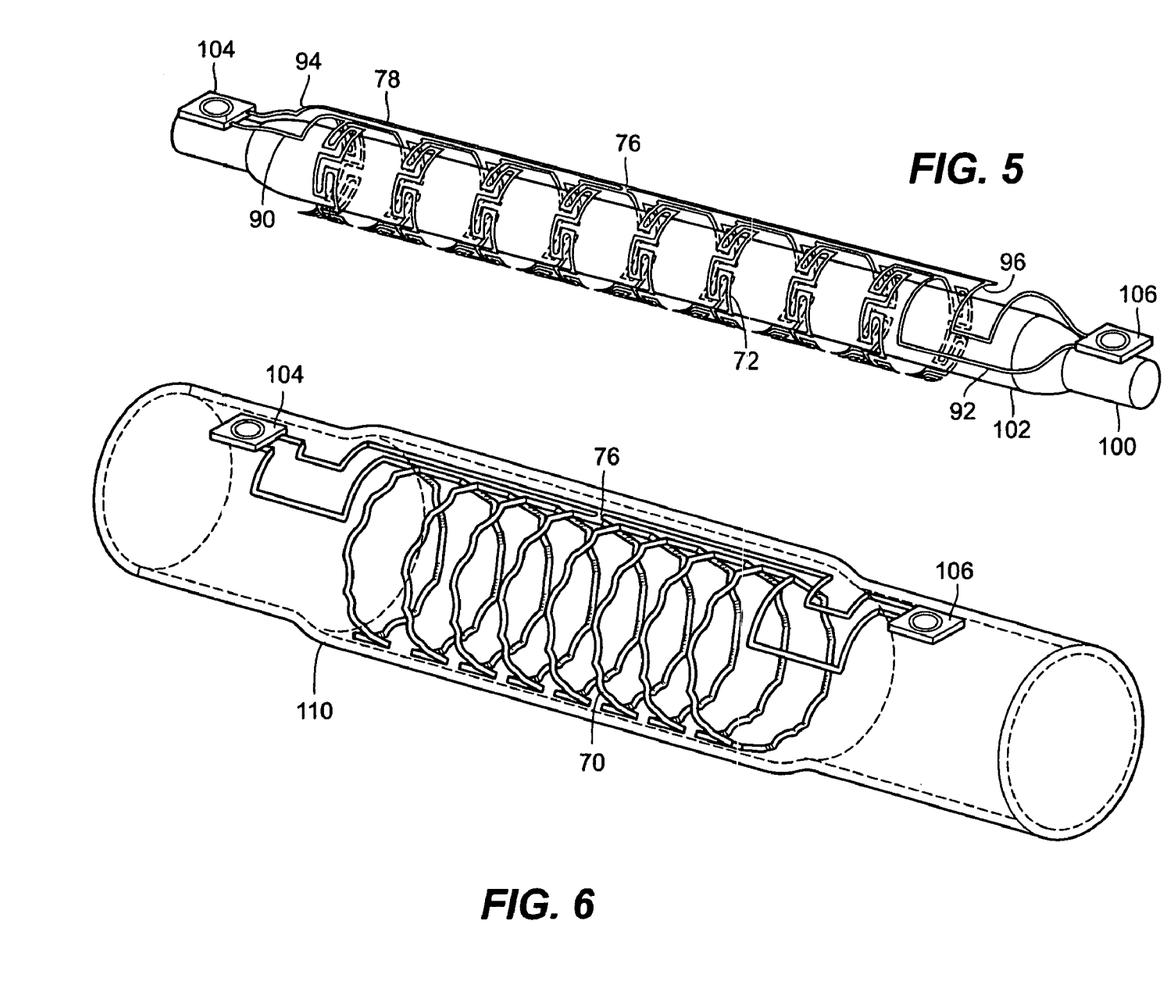
FIG. 5 is a schematic representation of the stent device of FIG. 3 prior to catheter-based deployment.
FIG. 6 is a perspective illustration of the stent device of FIG. 3 after catheter-based deployment in a mock artery; and, FIGS. 7A-7E are schematic, cross-sectional representations of a portion of the stent device of FIG. 3 during a fabrication sequence.

The scaffolding component of the dual-inductor stent device 50 according to one embodiment is shown in greater detail in FIGS. 4 and 5 prior to deployment. In this case, a stent device 70 is a planar device prior to plastic deformation and, thus, can be fabricated from a planar metal sheet. As mentioned previously, however, alternative embodiments include forming the device 50 from a tubular foil. In either case, the device 70 has a series of cross bands 72 comprised of, for example, 50 μm-wide involute beams 74, with a single bridge or link 76 to a longitudinal beam 78 at or near the center of the device 70. The involute bands 72 form two separate inductors 80 and 82, and the beam 78 acts as a common electrical node for both of the inductors 80 and 82. At each longitudinal end of the device, the bands 72 terminate in a section that forms a ring 84. The rings 84 provide enhanced mechanical rigidity in the pre-expansion, pre-deployment state as it is assembled around the angioplasty balloon (see FIG. 5). The rings 84 also provide improved radial stiffness after expansion/deployment. To complete the two LC tanks, capacitive pressure sensors (see FIG. 5) are mounted on first and second platforms 86 and 88. The platforms 86 and 88 may be integrally formed with the rest of the device 70 and, as such, provide an electrical connection to the coils 80 and 82 via interconnects 90 and 92, respectively. The sensors are connected across the common electrical node via further interconnects 94 and 96 connected to the longitudinal beam 78, thereby implementing two L-C tanks when complete. In this manner, the longitudinal beam 78 acts as a convenient common electrical node for the components of both LC tank circuits, namely both inductors or coils 80 and 82, and both sensors.

It should be noted that, in an alternative embodiment, the device 50 may be modified to present a single-inductor helical structure, where the bridge 76 would be either moved, removed, or otherwise modified as appropriate. Alternatively, the single-inductor embodiment may have one or more links for connection of a longitudinal beam at, for instance, one of the rings 84 of the scaffolding structure. In either of the single-inductor or dual-inductor cases, however, the structural support of the device 50 is sufficient to avoid having to rely on two side beams having breakable links to form the helical portion (in contrast to the embodiment shown in FIGS. 2A-D). Nonetheless, in an alternative embodiment, breakable or other links may be added to the longitudinal beam 78 or other portions of the structure, as desired, to increase structural support prior to deployment or expansion.

When a liquid flows through a channel, there is a pressure drop between two separate locations that depends on the flow rate. A general expression for this drop for steady-state flow is:

$$P_2 - P_1 = R_a V + R_b V^2 \qquad (1)$$

where $P_1$ and $P_2$ are pressures at downstream and upstream locations respectively, V is area-averaged flow velocity in an unobstructed vessel, and $R_a$ and $R_b$ are coefficients that depend on obstacle geometry and fluid properties. The first term is associated with a loss due to viscous shearing stress, and the second is due to geometry variation inside a channel, which includes re-deposited plaque or excess tissue grown over a stent. As the obstacles grow, the non-linear term dominates. The dual-inductor design is intended to implement sensing based on this relationship.

During the deployment of a stent, the scaffolding structure is generally pushed against the walls of a blood vessel, and it is necessary to protect the micromachined pressure sensors from physical damage or unpredictable characteristic changes because of the application of the radial force. Having the platforms 86 and 88 for the sensors in the stent device 70 provides a rigid bonding site and also helps to protect the sensors from bending forces. For example, several preliminary experiments were conducted with samples of the device 70 that were pressurized by a balloon inside a 3-mm i.d. silicone mock artery, which was designed to evaluate vascular implants and had compliance similar to human artery (Dynatek-Dalta, Inc., MO). The device samples showed, in fact, that the sensors had no damage and were still functioning even after full expansion to 3.5-mm diameter. However, in order to minimize any potential failures, as shown in FIGS. 4 and 5, the stent device 70 was designed to locate the sensors outside of the length of the angioplasty balloon, that, in this sample case, had a length of 16-mm length. As a result, the platforms 86 and 88 for the sensors are outside of the structural support provided by the rings 84. This design concept of locating the sensor at an end of the device, past the length of the angioplasty balloon, and perhaps outside of the support structure, may also be applied to other embodiments, such as the single-sensor embodiment of FIGS. 2A-D.

Disposing the sensor platforms 86 and 88 and, therefore, the sensors, at longitudinal ends of the stent device provides advantages beyond protecting the sensors from damage due to an expanding deployment device or other damages during deployment or operation. The large separation between the sensors also helps to increase the first term in equation (1) and, therefore improves the quality of the intraluminal measurements.

FIG. 5 shows the stent device 70 according to the embodiment of FIG. 4 after a catheter 100 and a deployment balloon 102 carried by the catheter 100 have been threaded through the coils 80 and 82, and the rings 84, such that the bands alternate above and below the balloon 102 as described and shown above. Again, like elements are identified with like reference numerals. Shown in FIG. 5, however, are first and second capacitive pressure sensors 104 and 106 as mounted on the platforms 86 and 88, respectively. The sensors 104 and 106 may be of the same type as the sensor used in connection with the embodiments of FIGS. 1 and 2A-D and, more generally, take any one of a number of micromachined or other forms known to those skilled in the art. For instance, one or both of the pressure sensors 104 and 106 may be constructed in accordance with the teachings of DeHennis et al., "A Double-Sided Single-Chip Wireless Pressure Sensor," Proc. IEEE MEMS 2002, pp. 252-255 (2002), and Akar et al., "A Wireless Batch Sealed Absolute Capacitive Pressure Sensor," Sensors and Actuators A, 95, pp. 29-38 (2001), the disclosures of which are hereby incorporated by reference in their entirety. The sensors 104 and 106 may, but need not, be identical. Furthermore, in alternative embodiments, the sensors 104 and 106 need not both be pressure sensors. Further details regarding the pressure sensors 104 and 106 of two exemplary embodiments may be found in the Examples to follow.

FIG. 6 shows the stent device 70 after deployment in a mock artery 110 filled with DI water. The angioplasty balloon 102 has been removed, leaving the pressure sensors 104 and 106 disposed along interior walls of the artery 110. The inflation of the balloon 102 causes the artery 110, which has 0.25-mm thick walls, to expand from 3.0 mm to 3.5 mm i.d. It can be seen that during this inflation process, the two sensors 104 and 106 are located just off the pressurized range, reducing physical impact to both the sensors and the blood vessel. Upon inflation, the deployed device 70 is permanently deformed from planar to helical shape, which consists of two separate coils with 3 and 3.5 turns in this case.

Figure 7A:
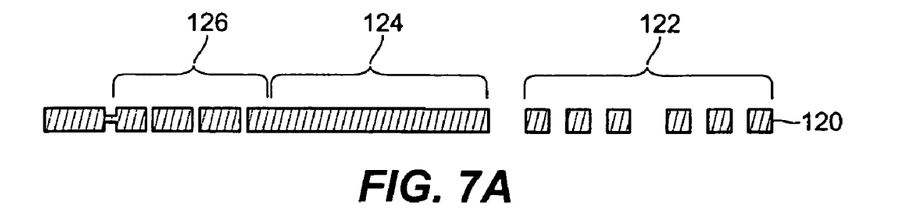
Figure 7B:
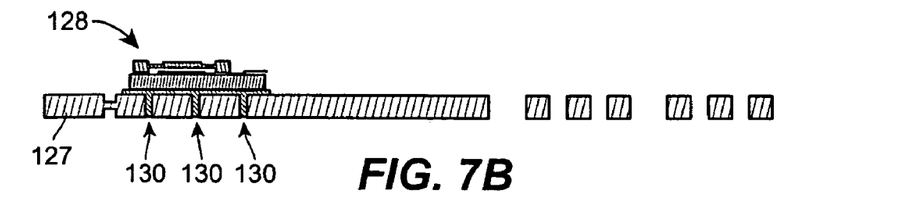
Figure 7C:
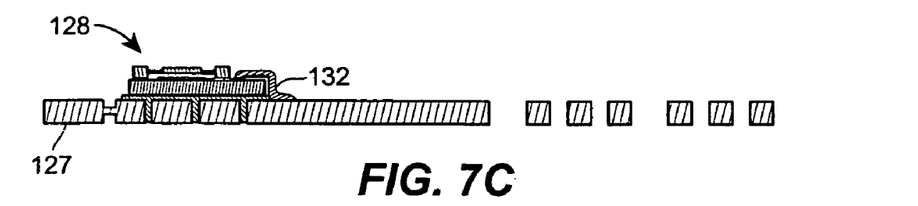
Figure 7D:
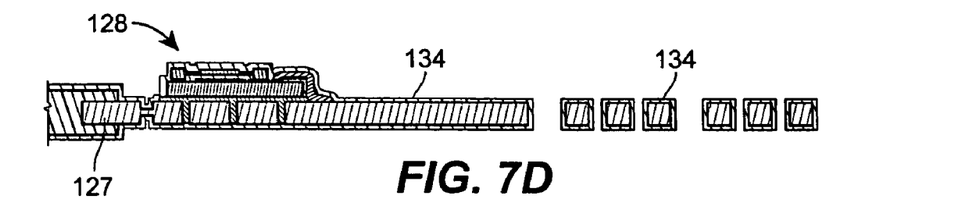
Figure 7E:
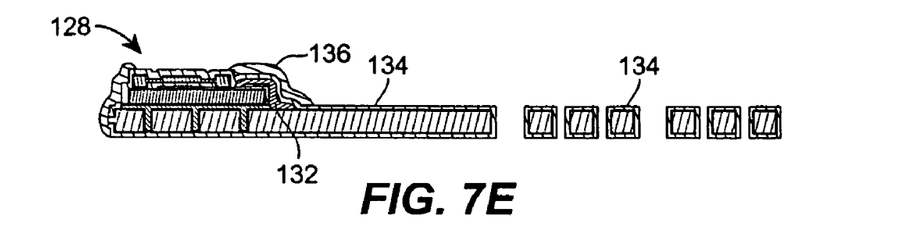

FIGS. 7A-7E show the process flow involved in the fabrication of the exemplary embodiment of FIGS. 4-6, as well as one that can also be adapted for the manufacture of other embodiments. More particularly, the process flow is broken into fabrication steps shown for the device 70 in a cross-sectional view of a portion of the device shown in FIG. 4. With reference first to FIG. 7A, a pattern is created by µEDM of a 50-µm thick #304 stainless steel sheet 120. The patterned sheet 120 includes a band portion 122, an interconnect portion 124, and a sensor platform portion 126. At this point, the machined structure may remain connected to the original sheet (shown as holder portion 127) for ease of handling during following steps. One or more pressure sensors indicated generally at 128 and fabricated on a 500-µm thick glass substrate are diced to 1.4×1.8 mm² chips in advance. With reference now to FIG. 7B, the sensors 128 are attached to the platform portion 126 of the patterned sheet 120, which, as described above are attached at the ends of the longitudinal beam 78 (and associated interconnects 94 and 96) from the rings 84. The bonding may be performed with enamel, which offers good adhesion and mechanical strength, and it is also easily applied and cured rapidly. Perforations indicated generally at 130 in the platform portion 126 serve as escape paths for excess enamel. Next, as shown in FIG. 7C, the sensors 128 are then electrically connected to the interconnects 90, 92, 94, 96 with a conductive adhesive 132. The device 70 is then coated with a 0.5-μm thick parylene layer 134 everywhere for electrical insulation, as shown in FIG. 7D. All surfaces of the device 70 are coated. With reference to FIG. 7E, the device 70 is then mechanically released from the sheet (or holder portion 127). Finally, an additional epoxy layer 136 is applied to a perimeter of the sensors 128 for enhancing the bonding strength.

One advantageous feature of the fabrication process described above is that the resulting structure includes multiple interconnects, platforms, and extendible bands that are all formed from a single, continuous, conductive sheet. The sheet is planar in the embodiment described, but may alternatively be tubular in shape prior to laser-based machining or other fabrication processes.

EXAMPLES

The following examples are provided to illustrate the invention, but are not intended to limit the scope thereof. Example 1 corresponds with a single-inductor, single-sensor embodiment, such as the embodiment described and shown in connection with FIGS. 1 and 2A-D. Example 2 presents a dual-inductor, dual-sensor embodiment, such as the embodiment described and shown in connection with FIGS. 3-6.

Example 1

As an initial matter, it should be noted that, for an effective wireless link, minimal damping is desired in the LC tank. The quality factor is expressed as:

$$Q \approx \frac{1}{R_{STp}} \sqrt{\frac{L_{ST}}{C_{SE} + C_{STp}}}$$

where $L_{ST}$ is inductance of the stent device, $C_{SE}$ is capacitance of the sensor, $C_{STp}$ is parasitic capacitance, and $R_{STp}$ is parasitic resistance. The impact of the $R_{STp}$ is greater than that of $C_{STp}$. The parasitic resistance contributed by the stent inductance is inversely related to the beam cross-section, whereas the parasitic capacitance that it contributes is proportional to the beam surface area. Therefore, $R_{STp}$ depends on the square of the beam diameter whereas $C_{STp}$ is simply proportional to it. Thus, it is electrically favorable to increase the thickness of the beams. In fact, this is favorable mechanically as well, because it would increase the radial stiffness of the stent. However, from the biological viewpoint, increasing the volume of the structural elements can be undesirable, which may warrant application-specific designs and structural optimization.

The micromachined pressure sensor that was used in these examples consisted of a vacuum-sealed cavity capped by a 3.7-μm thick $p^{++}$ Si circular diaphragm with the 1-mm diameter and 5-μm gap. The diaphragm had a 10-μm thick boss with varied diameter for providing different dynamic range and an oxide layer on the backside for electrical protection in case of a contact between the diaphragm and a bottom electrode. The sensors were fabricated by a silicon-on-glass dissolved wafer process. The fabrication was combined with a reflowed Si—Au eutectic bonding technique for achieving low-impedance interconnect (Ti:50 nm/Pt:80 nm/Au:150 nm) to the sealed sensor.

As described herein above, the micromachined stent serves as an antenna for wireless monitoring of implantable microsensors. In this example, the stent has a 4 mm long, 3.5 mm diameter design fabricated from 50 μm thick stainless steel foil using a batch-compatible micro electro-discharge machining process. As it is expanded during deployment, the stent transforms from a mesh that fits snugly around the angioplasty balloon into an inductive coil. This is accomplished by strategically located breakable links which change its electrical characteristics during the plastic deformation into its final shape. This 20 nH coil is coupled to a capacitive pressure microsensor that is approximately $1.2 \times 1.4 \times 0.5$ mm$^3$ in dimensions. Wireless monitoring is demonstrated by showing that the resonant electrical loading provided by this LC tank to a separate transmitting coil shifts by 400 kHz over a pressure change of 800 Torr. The tests were performed in a liquid environment.

The stent device was tested and characterized for both electrical and mechanical response. The electrical tests were performed under both dry and wet conditions: in air below atmospheric pressure (Test A); and in liquid elevated pressures comparable to those encountered in arteries (Test B). A non-conductive liquid was used in these preliminary measurements. The test set-up involved connecting the stent device in parallel to the capacitive pressure sensor, both located in a pressure-controlled chamber. The capacitance of the pressure sensor varied as the pressure was varied, with the input impedance Zin of the external coil monitored with an HP 4195 spectrum analyzer. The characteristics of the elements used in each experiment are set forth in the table below:

|  | Pressure sensor (at 760 Torr) | | Primary/external coil | |
| --- | --- | --- | --- | --- |
|  | Capacitance | Sensitivity | Diameter | Inductance |
| Test A: | 20 pF | 5.4 fF/Torr | 20 mm | 1.5 μH |
| Test B: | 17 pF | 5.0 fF/Torr | 10 mm | 0.3 μH |

For the dry measurements (Test A), a self-resonant peak in $Z_{in}$—located nominally at 57.7 MHz—shifted by +170 kHz as the pressure changed by −615 Torr. Despite a relatively noisy signal, the shift in peaks could be easily resolved because the measured Q of the resonant peak was about 115. The dependence of the resonant frequency on the pressure demonstrates an approximately linear response of 274 Hz/Torr. The nominal resonant frequency in the wet tests under Test B was 201 MHz. This differed from Test A because a different primary coil was used. The frequency was shifted by −760 kHz with pressure change of +1380 Torr. The pressure response was 500 Hz/Torr in this case.

A mechanical loading test was performed for assessing radial strength of the stent device. A 4-mm long sample was clipped on a z-stage and compressed radially by a micrometer against a fixed force gauge (Imada DPS-1). The measured response showed elastic behavior over a deflection range of 400 μm and a stiffness of 225 N/m. While the radial strength of this stent has been somewhat lower than certain commercially available stents, it is worth noting that, at 50 μm, the thickness of the steel foil used for these devices is half that used for many commercial stents, so it is easy to increase. As noted above, practice of the disclosed device is certainly not limited to a particular material or foil shape, much less a foil thickness.

Example 2

This example presents a micromachined antenna stent device that is integrated with two implantable microsensors for wireless sensing of blood flow and pressure with no battery. A device that has 20-mm length and 3.5-mm diameter (after expansion) is fabricated from 50 μm thick stainless steel foil by using batch-compatible micro-electro-discharge machining. This is coupled to two micromachined capacitive pressure sensors of approximately 1.4×1.8×0.5 mm$^3$ dimensions. A 0.5-μm thick parylene layer provides electrical insulation. The integrated device is deployed inside a silicone mock artery with a standard angioplasty balloon. The planar structure is plastically deformed to a tubular shape, resulting in dual helical coils with 50-60 nH each. These L-C tanks are used to wirelessly probe pressures at two points along a channel for flow-rate detection. Fluidic experiments that emulate a blockage in the mock artery demonstrate that the resonant impedance and phase provided by the LC-tanks to a separate transmitting coil shift by 5-40 MHz over flow-rate change of 150-300 mL/min. Pressure sensitivity is 273 ppm/Torr.

The micromachined pressure sensor consists of a vacuum-sealed cavity capped by a 3.7-μm thick p$^{++}$ Si circular diaphragm with the 1-mm diameter and 5-μm gap. The diaphragm had a 10-μm thick boss for better linearity and an oxide layer on the backside for electrical protection in case of a contact between the diaphragm and a bottom electrode. The sensors were fabricated on 500-μm thick glass substrates by a silicon-on-glass dissolved wafer process. The glass substrate of a pressure sensor that is placed at upstream of flow was thinned by wet etching down to 100 μm in order to achieve smoother flow and reduce force applied to the sensor that causes bending of the longitudinal beams which hold the sensor.

Although passive stents that use steel do not require any insulation, in this case the stent plays an electrical role as well. In addition the assembly includes micromachined pressure sensors. Thus, the two primary goals include biological and electrical protection. The former involves biocompatibilities of surface materials to tissues and blood. The latter involves two types of insulation; (1) between cross bands after expansion that could contact each other due to non-uniform expansion of the balloon, and (2) between the whole device and a surrounding fluid, i.e., blood, which is electrically conductive. Parylene-C was chosen for achieving these requirements because it has suitable characteristics. It provides a thin, uniform and conformal coating that is non-conductive, chemically inert, and biocompatible. It also has a proven history for applications for biomedical devices including cardiac stents.

In the fluidic test set-up used to evaluate the device, a pump/flow-controller regulates the flow (of DI water), and a separate meter (Validyne PS309) measures the pressure drop along the 8 cm-long artery. To simulate blockage due to plaque, a dielectric rod with 1.5-mm diameter is positioned inside the stent device. Input impedance and phase of an external coil are monitored with a HP4195 spectrum analyzer. The stent device inductance is approximately 110 nH in total. The pressure sensors have a measured response of ~6 fF/Torr, which reduces to ~2 fF/Torr with a 1.3-μm thick parylene coating. The first sensor, which had lower capacitance is coupled to the 3-turn inductor, and the second sensor is paired with the 3.5-turn inductor, so that these L-C tanks have different resonant frequencies.

An impedance peak nominally at 239.1 MHz in a 4-mm diameter external coil with inductance of 610 nH is shifted down by increasing flow rate, with a corresponding differential pressure drop with 9-31 kHz reduction per mL/min. increase in the flow range over 370 mL/min. (Typical coronary artery flow is 100-200 mL/min.) The pressure response observed is 57.4 kHz/Torr (at gauge pressure of 113 Torr), corresponding sensitivity is 273 ppm/Torr. A phase peak, which occurs nominally near 350 MHz with a different external coil, drops in frequency by 152-569 kHz per mL/min. increase in flow. In the absence of the regulation rod, the shift is only 25-42 kHz per mL/min. As expected, the absence of this blockage has a marked impact.

Wireless acquisition of pressure has been demonstrated using a micromachined stent device with a capacitive pressure sensor, validating the concept of using stents as antennas for microsensors. A 20 nH stent device with 4-mm length, 3.5-mm diameter and 50-μm thickness was coupled to a capacitive pressure sensor with dimensions of 1.2×1.4×0.5 mm$^3$ and sensitivity of 5 fF/Torr. In accordance with one embodiment, a design was demonstrated that exploits the use of strategically placed breakable links that were severed by stress concentrations during inflation of the angioplasty balloon. This design may also be extended to other micromachined components such 3D coils and transformers for RF communication. Telemetrically powered implantable devices, such as a muscular stimulator and a neural recoding system sensor may also benefit from this technology.

In accordance with another embodiment, a wireless implantable system for sensing flow and pressure inside a blood vessel has been presented. A 110-nH dual-inductor stent device with 20-mm length, 3.5-mm diameter, and 50-μm thickness was integrated with two micromachined capacitive pressure sensors with dimension of 1.4×1.8×0.5 mm$^3$ and sensitivity of 6 fF/Torr. The whole device was designed to be compatible with standard stenting tools and procedures, and it was successfully deployed inside a mock artery by the inflation of an angioplasty balloon. Telemetry tests revealed capability for flow sensing and high pressure sensitivity. The design and fabrication of the stent device based on use of planar stainless steel foil and batch-compatible μEDM technology will permit easier incorporation of other planar-based technologies for further improvement of the performance.

The foregoing description is given for clearness of understanding only, and no unnecessary limitations should be understood therefrom, as modifications within the scope of the invention may be apparent to those having ordinary skill in the art.

Still other modifications and alternative embodiments will be apparent to those skilled in the art in view of the foregoing description. The description is to be construed as illustrative only, and is for the purpose of teaching those skilled in the art the best mode of carrying out the invention. The details of the structure and method may be varied substantially without departing from the spirit of the invention, and exclusive use of all modifications which come within the scope of the appended claims is reserved.

What is claimed is:

1. A stent device, comprising:
    a structure comprising a set of extendible bands that are capable of plastic deformation to form a scaffolding having an inductance, wherein the set of extendible bands has a non-helical configuration prior to the plastic deformation and wherein a portion of the non-helical configuration forms the scaffolding upon plastic deformation; and
    a capacitance electrically coupled to the set of extendible bands such that the capacitance and the inductance form a tank circuit after the plastic deformation of the set of extendible bands.

2. The stent device of claim 1, wherein the structure comprises a longitudinal beam coupled to the set of extendible bands.

3. The stent device of claim 2, wherein the longitudinal beam comprises a side beam having a reduced-width link between adjacent bands of the set of extendible bands such that the reduced-width link breaks a connection between the adjacent bands upon plastic deformation of the structure.

4. The stent device of claim 2, wherein the longitudinal beam and the set of extendible bands are directly connected by a single link.

5. The stent device of claim 2, wherein the structure comprises a further set of extendible bands such that the scaffolding comprises a further inductance, the stent device further comprising a further capacitance coupled to the further set of extendible bands such that the further capacitance and the further inductance form a further tank circuit after plastic deformation of the further set of extendible bands.

6. The stent device of claim 5, wherein the longitudinal beam is a common electrical node for the first-named inductance and the further named inductance and the first-named capacitance and the further named capacitance.

7. The stent device of claim 6, wherein the first-named capacitance and the further capacitance comprise first and second capacitive sensors, respectively, and wherein the first and second capacitive sensors are disposed at opposite ends of the longitudinal beam.

8. The stent device of claim 7, wherein the longitudinal beam has a length such that the opposite ends of the longitudinal beam are positioned beyond where an expandable deployment device is disposed during the plastic deformation of the structure.

9. The stent device of claim 8, wherein the structure comprises first and second platforms upon which the first and second capacitive sensors are mounted, respectively.

10. The stent device of claim 1, wherein the set of extendible bands comprises a non-conductive support and a conductive trace disposed on the non-conductive support.

11. The stent device of claim 1, wherein the scaffolding comprises a helix portion and a ring portion such that the ring portion provides structural support at an end of the helix portion.

12. The stent device of claim 1, wherein the non-helical configuration is planar such that each extendible band of the set of extendible bands comprises a plurality of involute, planar sections prior to plastic deformation.

13. The stent device of claim 1, wherein the non-helical configuration is tubular.

14. A device for maintaining patency of a lumen while monitoring an intraluminal characteristic of the lumen, comprising:
   a sensor responsive to the intraluminal characteristic of the lumen to generate a signal indicative thereof; and
   a stent structure having a non-tubular and non-helical configuration prior to deployment wherein the non-helical configuration of the stent structure is capable of plastic deformation to form a helical scaffolding upon deployment such that the helical scaffolding comprises an inductance coupled to the sensor for wireless transmission of the signal.

15. The device of claim 14, wherein the non-helical configuration comprises a planar set of involute bands.

16. The device of claim 14, wherein the non-helical configuration comprises a plurality of cross bands coupled via a beam having a breakable link for disconnecting adjacent cross bands of the plurality of cross bands upon deployment to form the helical scaffolding.

17. The device of claim 14, wherein the stent structure is further capable of plastic deformation to form a non-helical scaffolding structurally coupled to the helical scaffolding for maintaining the patency of the lumen.

18. The device of claim 17, wherein the non-helical scaffolding comprises a pair of rings coupled to the helical scaffolding at respective longitudinal ends of the helical scaffolding.

19. The device of claim 14, wherein the stent structure comprises a non-conductive support and a conductive trace disposed on the non-conductive support.

20. The device of claim 14, wherein the sensor is an upstream sensor, the stent device further comprises a downstream sensor, and the stent structure includes a further helical scaffolding dedicated to the downstream sensor such that the further helical scaffolding comprises a further inductance for wireless transmission of a signal generated by the downstream sensor.

21. The device of claim 20, wherein a longitudinal interconnect beam acts as a common electrical node for the upstream sensor, the downstream sensor, and the first-named inductance and the further inductance.

22. A device for maintaining patency of a lumen while monitoring an intraluminal characteristic of the lumen, comprising:
   a sensor responsive to the intraluminal characteristic of the lumen to generate a signal indicative thereof; and
   a scaffolding deployed in the lumen and having a helical portion and a non-helical portion wherein the helical portion comprises an inductance coupled to the sensor for wireless transmission of the signal and wherein the non-helical portion provides structural support for maintaining the patency of the lumen, wherein the scaffolding comprises a set of extendible bands, wherein the sensor is structurally coupled to the scaffolding.

23. The device of claim 22, wherein the scaffolding comprises a side beam having a plurality of broken links that disconnect adjacent bands of the set of extendible bands to form the helical portion.

24. The device of claim 22, wherein the non-helical portion comprises a pair of rings coupled to the helical portion at respective longitudinal ends of the helical portion.

25. The device of claim 24, wherein the sensor is longitudinally disposed outside of one of the pair of rings.

26. The device of claim 22, wherein the sensor is an upstream sensor, the device further comprising a downstream sensor responsive to a further intraluminal characteristic, and wherein the helical portion of the scaffolding comprises a further inductance coupled to the downstream sensor.

27. The device of claim 26, wherein each of the first-named inductance and the further inductance has a respective and differing number of coil turns for separate wireless transmission at different resonant frequencies.

28. The device of claim 26, wherein the scaffolding comprises a longitudinal beam coupled to the helical portion.

29. The device of claim 28, wherein the longitudinal beam acts as a common electrical node for the upstream and downstream sensors, and the first-named inductance and the further inductance.

30. The device of claim 29, wherein the upstream and downstream sensors comprise capacitive pressure sensors such that the first-named intraluminal characteristic is an upstream pressure and the further intraluminal characteristic is a downstream pressure.

31. The device of claim 22, wherein the helical portion comprises a non- conductive support and a conductive trace disposed on the non-conductive support.

32. The device of claim 22, wherein the helical and non-helical portions of the scaffolding are formed of a continuous tubular sheet.

33. A stent device for monitoring an intraluminal characteristic, comprising:
a plastically deformable structure capable of having a planar configuration prior to deformation and having a helical portion upon catheter-based deployment wherein the plastically deformable structure comprises a sensor site positioned at an end of the plastically deformable structure; and
a sensor capable of generating a signal indicative of the intraluminal characteristic wherein the sensor is structurally coupled to the plastically deformable structure at the sensor site such that the sensor is suitably disposed for the catheter-based deployment with the plastically deformable structure;
wherein the helical portion comprises an inductance coupled to the sensor to enable wireless transmission of the signal generated by the sensor.

34. The stent device of claim 33, wherein the plastically deformable structure comprises a longitudinal beam and the end is located at a termination point of the longitudinal beam.

35. The stent device of claim 33, wherein the end lies beyond an extent reached by an inflatable deployment device used during the catheter-based deployment.

36. The stent device of claim 33, wherein the sensor site comprises a platform upon which the sensor is mounted.

37. The stent device of claim 36, wherein the plastically deformable structure and the platform are formed of a continuous, conductive sheet such that the plastically deformable structure is capable of residing in a non-helical profile that enables catheter-based deployment.

38. The stent device of claim 37, wherein the platform and the sensor are rigidly bonded such that the sensor is protected from damage from bending forces experienced during the catheter-based deployment.

39. The stent device of claim 33, wherein the end is an upstream end and the sensor is an upstream sensor, the stent device further comprising a downstream sensor disposed at a further sensor site positioned at a downstream end of the plastically deformable structure.

40. The stent device of claim 39, wherein the plastically deformable structure comprises first and second inductive coils coupled to the upstream and downstream sensors, respectively.

41. The stent device of claim 40, wherein the plastically deformable structure comprises a longitudinal beam, and wherein the longitudinal beam acts as a common node electrical node for the upstream sensor, the downstream sensor, and the first and second inductive coils.

42. The stent device of claim 41, wherein the plastically deformable structure comprises first and second rings coupled to ends of the first and second inductive coils, respectively.

43. The stent device of claim 42, wherein the first and second inductive coils comprise first and second sets of extendible bands, respectively.

44. The stent device of claim 33, wherein the helical portion comprises a non-conductive support and a conductive trace disposed on the non-conductive support.

45. The stent device of claim 33, wherein the plastically deformable structure is formed of a continuous tubular sheet.

46. A stent device for monitoring first and second intraluminal characteristics, comprising:
first and second sensors generating respective signals indicative of the first and second intraluminal characteristics, respectively; and
a scaffolding comprising first and second inductive coils respectively coupled to the first and second sensors for separate, wireless transmission of the respective signals indicative of the first and second intraluminal characteristics, wherein the first and second inductive coils comprise a plurality of extendible bands and wherein the scaffolding comprises a common electrical node and a connection between the plurality of extendible bands and the common electrical node, the connection defining first and second sets of extendible bands of the plurality of extendible bands wherein the first and second sets of extendible bands form the first and second inductive coils, respectively.

47. The stent device of claim 46, wherein the scaffolding comprises a longitudinal interconnect beam that acts as the common electrical node for the first and second sensors and the first and second inductive coils.

48. The stent device of claim 46, further comprising first and second platforms upon which the first and second sensors are mounted, respectively, and wherein the first and second platforms are spaced upstream and downstream from the scaffolding via first and second interconnects, respectively.

49. The stent device of claim 48, wherein the first and second coils, the first and second interconnects, and the first and second platforms are formed of a continuous, conductive sheet.

50. The stent device of claim 49, wherein the continuous, conductive sheet has a tubular shape prior to deployment.

51. The stent device of claim 46, wherein the scaffolding comprises first and second rings coupled to ends of the first and second inductive coils, respectively.

52. The stent device of claim 46, wherein the plurality of extendible bands are capable plastic deformation.

53. The stent device of claim 52, wherein the connection is not centered such that the first and second sets of extendible bands have a differing number of turns and a differing inductance level, and further such that the respective signals indicative of the first and second intraluminal characteristics are transmitted at different frequencies.

54. The stent device of claim 46, wherein the first and second sensors comprise respective pressure sensors such that the first and second intraluminal characteristics comprise upstream and downstream intraluminal pressures.

55. The stent device of claim 46, wherein the scaffolding comprises a non-conductive support and a conductive trace disposed on the non-conductive support.

56. A stent device, comprising:
a plurality of bands capable of arrangement in a planar structure and plastic deformation into a 3-D structure, wherein the plurality of bands comprises first and second adjacent bands;
wherein the plastic deformation of the first and second adjacent bands involves expansion in first and second directions, respectively; and,
wherein the first and second adjacent bands are coupled such that the expansion in the first and second directions arranges the first and second adjacent bands in a helical coil.

57. The stent device of claim 56, further comprising a longitudinal beam coupled to the plurality of bands.

58. The stent device of claim 56, wherein each band of the plurality of bands has a set of involute sections such that each band is extendible during the expansion.

59. The stent device of claim 56, wherein the plurality of bands comprises a pair of bands coupled to the helical coil at an end thereof and arranged in a ring of the 3-D structure after the expansion of the planar structure.

60. The stent device of claim 56, further comprising a capacitance coupled to the helical coil such that the capacitance and an inductance of the helical coil form a tank circuit.

61. The stent device of claim 60, wherein the capacitance comprises a capacitive pressure sensor.

* * * * *